United States Patent
Gonzalez-Hernandez (10) Patent No.: US 9,956,017 B2
(45) Date of Patent: May 1, 2018

(54) BONE PLATE FOR PLATE OSTEOSYNTHESIS AND METHOD FOR USE THEREOF

(71) Applicant: TOBY ORTHOPAEDICS, INC., Miami, FL (US)

(72) Inventor: Eduardo Gonzalez-Hernandez, Miami, FL (US)

(73) Assignee: TOBY ORTHOPAEDICS, INC., Miami, FL (US)

( * ) Notice: Subject to any disclaimer, the term of this patent is extended or adjusted under 35 U.S.C. 154(b) by 228 days.

(21) Appl. No.: 15/070,729

(22) Filed: Mar. 15, 2016

(65) Prior Publication Data
US 2016/0192971 A1    Jul. 7, 2016

Related U.S. Application Data

(62) Division of application No. 13/840,194, filed on Mar. 15, 2013, now Pat. No. 9,283,008.

(60) Provisional application No. 61/738,141, filed on Dec. 17, 2012.

(51) Int. Cl.
A61B 17/80    (2006.01)
A61B 17/68    (2006.01)

(52) U.S. Cl.
CPC .......... *A61B 17/8085* (2013.01); *A61B 17/80* (2013.01); *A61B 2017/681* (2013.01)

(58) Field of Classification Search
CPC .. A61B 17/80; A61B 17/8061; A61B 17/8085
See application file for complete search history.

(56) References Cited

U.S. PATENT DOCUMENTS

| | | | |
|---|---|---|---|
| 1,950,799 | A | 3/1934 | Jones |
| 2,500,370 | A | 3/1950 | McKibbin |
| 2,555,291 | A | 5/1951 | Poupitch |
| 2,580,821 | A | 1/1952 | Toufick |
| 2,682,265 | A | 6/1954 | Collison |
| 2,853,114 | A | 9/1958 | Barry |
| 2,875,663 | A | 3/1959 | Wieber |
| 3,489,143 | A | 1/1970 | Halloran |
| 3,552,389 | A | 1/1971 | Allgower et al. |
| 3,579,831 | A | 5/1971 | Stevens et al. |
| 3,716,050 | A | 2/1973 | Johnston |

(Continued)

FOREIGN PATENT DOCUMENTS

| | | |
|---|---|---|
| DE | 86 28 766 U1 | 12/1986 |
| DE | 89 07 443 U1 | 9/1989 |

(Continued)

OTHER PUBLICATIONS

U.S. Appl. No. 10/993,723, filed Nov. 2004, Gonzalez-Hernandez.
(Continued)

*Primary Examiner* — Zade Coley
*Assistant Examiner* — Olivia C Chang
(74) *Attorney, Agent, or Firm* — Martin & Ferraro, LLP (57) ABSTRACT

A bone plate and method for use thereof affords use of at least two surgical approaches to attach the bone plate to a fractured bone to facilitate reduction and repair thereof. The bone plate includes two domains extending in different directions from a transition zone. The directions in which each of the two domains extend are generally opposite, and the transition zone is configured to afford portions of the two domains to be substantially disposed in planes that are transverse to one another.

6 Claims, 5 Drawing Sheets

(56) References Cited

U.S. PATENT DOCUMENTS

| | | |
|---|---|---|
| 3,791,380 A | 2/1974 | Dawidowski |
| 3,824,995 A | 7/1974 | Getscher et al. |
| 3,900,025 A | 8/1975 | Barnes, Jr. |
| 4,029,091 A | 6/1977 | von Bezold |
| 4,263,904 A | 4/1981 | Judet |
| 4,535,768 A | 8/1985 | Hourahane et al. |
| 4,683,878 A | 8/1987 | Carter |
| 4,733,654 A | 3/1988 | Marino |
| 4,776,330 A | 10/1988 | Chapman et al. |
| 4,790,302 A | 12/1988 | Colwill et al. |
| 4,794,919 A | 1/1989 | Nilsson |
| 4,796,612 A | 1/1989 | Reese |
| 4,838,264 A | 6/1989 | Bremer et al. |
| 4,858,602 A | 8/1989 | Seidel et al. |
| 4,870,957 A | 10/1989 | Goble et al. |
| 5,003,969 A | 4/1991 | Azer et al. |
| 5,015,248 A | 5/1991 | Burstein et al. |
| 5,041,113 A | 8/1991 | Biedermann et al. |
| 5,041,114 A | 8/1991 | Chapman et al. |
| 5,180,383 A | 1/1993 | Haydon |
| 5,190,544 A | 3/1993 | Chapman et al. |
| 5,324,291 A | 6/1994 | Ries et al. |
| 5,356,410 A | 10/1994 | Pennig |
| 5,364,399 A | 11/1994 | Lowery et al. |
| 5,423,860 A | 6/1995 | Lizardi et al. |
| 5,437,667 A | 8/1995 | Papierski et al. |
| 5,443,516 A | 8/1995 | Albrektsson et al. |
| 5,458,654 A | 10/1995 | Tepic |
| 5,462,547 A | 10/1995 | Weigum |
| 5,472,444 A | 12/1995 | Huebner et al. |
| 5,505,734 A | 4/1996 | Caniggia et al. |
| 5,578,035 A | 11/1996 | Lin |
| 5,584,835 A | 12/1996 | Greenfield |
| 5,586,985 A | 12/1996 | Putnam et al. |
| 5,601,553 A | 2/1997 | Trebing et al. |
| 5,620,449 A | 4/1997 | Faccioli et al. |
| 5,658,287 A | 8/1997 | Hofmann et al. |
| 5,665,088 A | 9/1997 | Gil et al. |
| 5,674,222 A | 10/1997 | Berger et al. |
| 5,676,667 A | 10/1997 | Hausman |
| 5,681,311 A | 10/1997 | Foley et al. |
| 5,709,686 A | 1/1998 | Talos et al. |
| 5,749,872 A | 5/1998 | Kyle et al. |
| 5,766,174 A | 6/1998 | Perry |
| 5,776,194 A | 7/1998 | Mikol et al. |
| 5,779,704 A | 7/1998 | Kim |
| 5,785,712 A | 7/1998 | Runciman et al. |
| 5,840,078 A | 11/1998 | Yerys |
| 5,868,749 A | 2/1999 | Reed |
| 5,931,839 A | 8/1999 | Medoff |
| 5,976,139 A | 11/1999 | Bramlet |
| 5,980,575 A | 11/1999 | Albrektsson et al. |
| 6,030,389 A | 2/2000 | Wagner et al. |
| 6,096,040 A | 8/2000 | Esser |
| 6,149,653 A | 11/2000 | Deslauriers |
| 6,152,927 A | 11/2000 | Farris et al. |
| 6,200,330 B1 | 3/2001 | Benderev et al. |
| 6,206,881 B1 | 3/2001 | Frigg et al. |
| D443,060 S | 5/2001 | Benirschke et al. |
| 6,270,499 B1 | 8/2001 | Leu et al. |
| D449,692 S | 10/2001 | Michelson |
| 6,302,887 B1 | 10/2001 | Spranza et al. |
| 6,331,179 B1 | 12/2001 | Freid et al. |
| 6,348,052 B1 | 2/2002 | Sammarco |
| 6,358,250 B1 | 3/2002 | Orbay |
| 6,364,881 B1 | 4/2002 | Apgar et al. |
| 6,364,882 B1 | 4/2002 | Orbay |
| 6,379,359 B1 | 4/2002 | Dahners |
| 6,398,783 B1 | 6/2002 | Michelson |
| 6,406,478 B1 | 6/2002 | Kuo |
| 6,409,768 B1 | 6/2002 | Tepic et al. |
| 6,413,259 B1 | 7/2002 | Lyons et al. |
| 6,440,135 B2 | 8/2002 | Orbay et al. |
| 6,468,278 B1 | 10/2002 | Muckter |
| 6,572,620 B1 | 6/2003 | Schon et al. |
| 6,620,195 B2 | 9/2003 | Goble et al. |
| 6,623,486 B1 | 9/2003 | Weaver et al. |
| 6,663,669 B1 | 12/2003 | Reiley |
| 6,669,701 B2 | 12/2003 | Steiner et al. |
| 6,695,844 B2 | 2/2004 | Bramlet et al. |
| 6,706,046 B2 | 3/2004 | Orbay et al. |
| 6,712,820 B2 | 3/2004 | Orbay |
| 6,719,759 B2 | 4/2004 | Wagner et al. |
| 6,730,090 B2 | 5/2004 | Orbay et al. |
| 6,776,781 B1 | 8/2004 | Uwaydah |
| 6,863,671 B1 | 3/2005 | Strobel et al. |
| 6,866,665 B2 | 3/2005 | Orbay |
| 6,916,323 B2 | 7/2005 | Kitchens |
| 6,945,973 B2 | 9/2005 | Bray |
| 7,001,388 B2 | 2/2006 | Orbay et al. |
| 7,063,701 B2 | 6/2006 | Michelson |
| 7,128,744 B2 | 10/2006 | Weaver et al. |
| D536,453 S | 2/2007 | Young et al. |
| 7,220,246 B2 | 5/2007 | Raulerson et al. |
| 7,229,444 B2 | 6/2007 | Boyd |
| 7,229,445 B2 | 6/2007 | Hayeck et al. |
| 7,235,079 B2 | 6/2007 | Jensen et al. |
| 7,354,441 B2 | 4/2008 | Frigg |
| 7,500,983 B1 | 3/2009 | Kaiser et al. |
| 7,563,263 B2 | 7/2009 | Orbay et al. |
| 7,582,107 B2 | 9/2009 | Trail et al. |
| 7,591,823 B2 | 9/2009 | Tipirneni |
| 7,604,657 B2 | 10/2009 | Orbay et al. |
| 7,637,908 B1 | 12/2009 | Gonzalez-Hernandez |
| 7,651,517 B2 | 1/2010 | Konieczynski et al. |
| 7,655,029 B2 | 2/2010 | Niederberger et al. |
| 7,695,472 B2 | 4/2010 | Young |
| 7,722,653 B2 | 5/2010 | Young et al. |
| 7,740,648 B2 | 6/2010 | Young et al. |
| 7,744,638 B2 | 6/2010 | Orbay |
| 7,776,076 B2 | 8/2010 | Grady, Jr. et al. |
| 7,780,667 B2 | 8/2010 | Watanabe et al. |
| 7,780,710 B2 | 8/2010 | Orbay et al. |
| 7,896,886 B2 | 3/2011 | Orbay et al. |
| 7,909,859 B2 | 3/2011 | Mosca et al. |
| 7,914,532 B2 | 3/2011 | Shaver et al. |
| 7,927,341 B2 | 4/2011 | Orbay et al. |
| 7,938,850 B2 | 5/2011 | Orbay et al. |
| 7,951,176 B2 | 5/2011 | Grady et al. |
| 7,951,178 B2 | 5/2011 | Jensen |
| 7,955,364 B2 | 6/2011 | Ziolo et al. |
| D643,121 S | 8/2011 | Milford et al. |
| 8,021,402 B2 | 9/2011 | Martin et al. |
| D646,785 S | 10/2011 | Milford |
| 8,062,296 B2 | 11/2011 | Orbay et al. |
| 8,062,367 B2 | 11/2011 | Kirschman |
| 8,100,953 B2 | 1/2012 | White et al. |
| 8,182,485 B1 | 5/2012 | Gonzalez-Hernandez |
| 8,317,842 B2 | 11/2012 | Graham et al. |
| 8,361,075 B2 | 1/2013 | Gonzalez-Hernandez |
| 8,469,999 B2 | 6/2013 | Gonzalez-Hernandez |
| 8,523,902 B2 | 9/2013 | Heaven et al. |
| 8,556,946 B2 | 10/2013 | Prandi |
| 8,574,234 B2 | 11/2013 | Gonzalez-Hernandez |
| 8,597,363 B2 | 12/2013 | Liverneaux et al. |
| 8,603,091 B2 | 12/2013 | Lutz |
| 8,608,783 B2 | 12/2013 | Graham |
| 8,690,916 B2 | 4/2014 | Gonzalez-Hernandez |
| 8,728,126 B2 | 5/2014 | Steffen |
| 8,764,808 B2 | 7/2014 | Gonzalez-Hernandez |
| 8,870,963 B2 | 10/2014 | Gonzalez-Hernandez |
| 8,906,070 B2 | 12/2014 | Medoff |
| 8,961,573 B2 | 2/2015 | Gonzalez-Hernandez |
| 9,254,154 B2 | 2/2016 | Gonzalez-Hernandez |
| 9,271,772 B2 | 3/2016 | Gonzalez-Hernandez |
| 9,271,776 B2 | 3/2016 | Gonzalez-Hernandez |
| 9,283,008 B2 | 3/2016 | Gonzalez-Hernandez |
| 2002/0091391 A1 | 7/2002 | Cole et al. |
| 2003/0135212 A1 | 7/2003 | Chow |
| 2003/0135216 A1 | 7/2003 | Sevrain |
| 2003/0208210 A1 | 11/2003 | Dreyfuss et al. |
| 2004/0097939 A1 | 5/2004 | Bonutti |
| 2004/0193278 A1 | 9/2004 | Maroney et al. |
| 2004/0199258 A1 | 10/2004 | Macara |

(56) References Cited

U.S. PATENT DOCUMENTS

| | | |
|---|---|---|
| 2004/0210220 A1 | 10/2004 | Tornier |
| 2005/0004574 A1 | 1/2005 | Muckter |
| 2005/0015089 A1 | 1/2005 | Young et al. |
| 2005/0021033 A1 | 1/2005 | Zeiler et al. |
| 2005/0038513 A1 | 2/2005 | Michelson |
| 2005/0085819 A1 | 4/2005 | Ellis et al. |
| 2005/0182405 A1 | 8/2005 | Orbay et al. |
| 2005/0240187 A1 | 10/2005 | Huebner et al. |
| 2005/0267476 A1 | 12/2005 | Chervitz et al. |
| 2005/0288681 A1 | 12/2005 | Klotz et al. |
| 2006/0015072 A1 | 1/2006 | Raulerson |
| 2006/0015101 A1 | 1/2006 | Warburton et al. |
| 2006/0058795 A1 | 3/2006 | Boyd |
| 2006/0106385 A1 | 5/2006 | Pennig |
| 2006/0161156 A1 | 7/2006 | Orbay |
| 2006/0217722 A1 | 9/2006 | Dutoit et al. |
| 2006/0229623 A1 | 10/2006 | Bonutti et al. |
| 2006/0235400 A1 | 10/2006 | Scheider |
| 2006/0241617 A1 | 10/2006 | Holloway et al. |
| 2006/0264947 A1 | 11/2006 | Orbay et al. |
| 2006/0264956 A1 | 11/2006 | Orbay et al. |
| 2006/0271105 A1 | 11/2006 | Foerster et al. |
| 2007/0005074 A1 | 1/2007 | Chudik |
| 2007/0016205 A1 | 1/2007 | Buetter et al. |
| 2007/0083207 A1 | 4/2007 | Ziolo et al. |
| 2007/0123880 A1 | 5/2007 | Medoff |
| 2007/0123885 A1 | 5/2007 | Kirschman |
| 2007/0162015 A1 | 7/2007 | Winquist et al. |
| 2007/0167953 A1 | 7/2007 | Prien et al. |
| 2007/0233113 A1 | 10/2007 | Kaelblein |
| 2007/0233114 A1 | 10/2007 | Bouman |
| 2007/0233115 A1 | 10/2007 | Sixto et al. |
| 2007/0265631 A1 | 11/2007 | Fox |
| 2008/0015593 A1 | 1/2008 | Pfefferle et al. |
| 2008/0045960 A1 | 2/2008 | Bruecker et al. |
| 2008/0119895 A1 | 5/2008 | Manceau |
| 2008/0132955 A1 | 6/2008 | Frigg |
| 2008/0140130 A1 | 6/2008 | Chan et al. |
| 2008/0154311 A1 | 6/2008 | Staeubli |
| 2008/0161853 A1 | 7/2008 | Arnold et al. |
| 2008/0161860 A1 | 7/2008 | Ahrens et al. |
| 2008/0161863 A1 | 7/2008 | Arnold et al. |
| 2008/0221577 A1 | 9/2008 | Elghazaly |
| 2008/0234749 A1 | 9/2008 | Forstein |
| 2008/0234752 A1 | 9/2008 | Dahners |
| 2008/0249572 A1 | 10/2008 | Tandon |
| 2009/0012571 A1 | 1/2009 | Perrow et al. |
| 2009/0024173 A1 | 1/2009 | Reis, Jr. |
| 2009/0048681 A1 | 2/2009 | Vlachos |
| 2009/0069851 A1 | 3/2009 | Gillard |
| 2009/0076554 A1 | 3/2009 | Huebner et al. |
| 2009/0105838 A1 | 4/2009 | Russo et al. |
| 2009/0118769 A1 | 5/2009 | Sixto, Jr. |
| 2009/0125070 A1 | 5/2009 | Sixto, Jr. et al. |
| 2009/0171399 A1 | 7/2009 | White et al. |
| 2009/0192550 A1 | 7/2009 | Leung et al. |
| 2009/0216270 A1 | 8/2009 | Humphrey |
| 2009/0228010 A1 | 9/2009 | Gonzalez-Hernandez et al. |
| 2009/0254089 A1 | 10/2009 | Tipirneni et al. |
| 2009/0254189 A1 | 10/2009 | Scheker |
| 2009/0264936 A1 | 10/2009 | Gonzalez-Hernandez et al. |
| 2009/0275987 A1 | 11/2009 | Graham et al. |
| 2009/0275991 A1 | 11/2009 | Medoff |
| 2009/0281577 A1 | 11/2009 | Graham et al. |
| 2009/0281578 A1 | 11/2009 | Spencer |
| 2009/0299369 A1 | 12/2009 | Orbay et al. |
| 2009/0306711 A1 | 12/2009 | Stone et al. |
| 2009/0312758 A1 | 12/2009 | Petit |
| 2009/0312760 A1 | 12/2009 | Forstein et al. |
| 2009/0312802 A1 | 12/2009 | Dasilva |
| 2009/0326591 A1 | 12/2009 | Spencer, Jr. |
| 2010/0030276 A1 | 2/2010 | Huebner et al. |
| 2010/0057086 A1 | 3/2010 | Price et al. |
| 2010/0094358 A1 | 4/2010 | Moore |
| 2010/0145339 A1 | 6/2010 | Steffen |
| 2010/0145397 A1 | 6/2010 | Overes et al. |
| 2010/0198258 A1 | 8/2010 | Heaven et al. |
| 2010/0217393 A1 | 8/2010 | Theofilos |
| 2010/0262194 A1 | 10/2010 | Wagner et al. |
| 2010/0324602 A1 | 12/2010 | Huebner et al. |
| 2010/0331844 A1 | 12/2010 | Ellis et al. |
| 2011/0152943 A1 | 6/2011 | Gonzalez-Hernandez |
| 2011/0160730 A1 | 6/2011 | Schonhardt et al. |
| 2011/0295324 A1 | 12/2011 | Donley |
| 2012/0226321 A1 | 9/2012 | Gonzalez-Hernandez |
| 2012/0226322 A1 | 9/2012 | Gonzalez-Hernandez |
| 2013/0116734 A1 | 5/2013 | Gonzalez-Hernandez |
| 2014/0121779 A1 | 5/2014 | Gonzalez-Hernandez |
| 2014/0180344 A1 | 6/2014 | Gonzalez-Hernandez |
| 2014/0277177 A1 | 9/2014 | Gonzalez-Hernandez |
| 2015/0045898 A1 | 2/2015 | Gonzalez-Hernandez |

FOREIGN PATENT DOCUMENTS

| | | |
|---|---|---|
| DE | 43 43 117 A1 | 6/1995 |
| DE | 198 57 279 A1 | 6/2000 |
| DE | 299 07 161 U1 | 8/2000 |
| EP | 0 551 588 A1 | 11/1992 |
| EP | 1 132 052 A2 | 9/2001 |
| EP | 1 468 655 A2 | 10/2004 |
| FR | 2 606 268 A1 | 5/1988 |
| FR | 2 680 673 A1 | 3/1993 |
| FR | 2 712 173 A1 | 5/1995 |
| JP | 4-138152 A | 5/1992 |
| WO | WO 99/38448 A1 | 8/1999 |
| WO | WO 02/071963 A1 | 9/2002 |
| WO | WO 2005/037117 A1 | 4/2005 |
| WO | WO 2008/007194 A2 | 1/2008 |
| WO | WO 2008/007196 A2 | 1/2008 |
| WO | WO 2012/003884 | 1/2012 |

OTHER PUBLICATIONS

U.S. Appl. No. 11/079,350, filed Mar. 2005, Gonzalez-Hernandez.
U.S. Appl. No. 11/366,676, filed Mar. 2006, Gonzalez-Hernandez.
U.S. Appl. No. 11/493,122, filed Jul. 2006, Gonzalez-Hernandez.
U.S. Appl. No. 11/526,331, filed Sep. 2006, Gonzalez-Hernandez.
U.S. Appl. No. 11/707,775, filed Feb. 2007, Gonzalez-Hernandez.
ACUMED; ACU-LOC Wrist Plating System; Jul. 2009; 20 pages.
ACUMED; The Mayo Clinic Congruent Elbow Plates (catalog); 2003; 19 pages.
ACUMED; The Mayo Clinic Congruent Elbow Plate System (catalog); Apr., 2006; 20 pages.
Christie, J., C.R. Howie and P.C. Armour, *Fixation of displaced subcapital femoral fractures. Compression screw fixation versus double divergent pins.* J Bone Joint Surg [Br] 1988; 70-B: 199-201.
Cross, W.M. et al., "Achieving stable fixation: biomechanical designs for fracture healing," AAOS Now (2008) 3 pages.
Guha, AR, et al.; "A New Technique of Fixation of Radial Head Fractures Using a Modified Tubular Plate," Journal of Postgraduate Medicine; Jul. 2004; vol. 50, Issue 2; pp. 113-114; Accessed Aug. 6, 2008 at: http://www.jpgmonline.com/article.asp?issn=0022-3859;year=2004;volume=50;issue=2;spage=113;epage=114;aulast=Guha.
Hand Innovations, LLC; DVR ANATOMIC, Volar Plating System; 2007; 4 pages.
Hussain M., R.N. Natarajan, A.H. Fayyazi, B.R. Braaksma, G.B. Andersson and H.S. An, *Screw angulation affects bone-screw stresses and bone graft load sharing in an anterior cervical corpectomy fusion with a rigid screw-plate construct: a finite element model study*; Spine Journal, vol. 9, Issue 12; Dec. 2009; pp. 1016-1023 (published online Oct. 12, 2009).
Lakatos, R. et al.; "General principles of internal fixation"; eMedicine; Aug. 2006; 51 pages.
"MIS Technique," published by Zimmer®, 1 page, prior to Nov. 19, 2004.
Postak, Paul D.; "Biomechanical Properties of Fixed-Angle Volar Distal Radius Plates Under Dynamic Loading;" 2007; 6 pages.
Robert, III, K.Q., R. Chandler, R,V, Barratta, K.A. Thomas and M.B. Harris, *The effect of divergent screw placement on the initial strength of plate-to-bone fixation.* J Trauma. Dec. 2003;55(6):1139-44.

(56) References Cited

OTHER PUBLICATIONS

Synthes, "Large Fragment LCP Instrument and Implant Set;" technique guide; 2003; 31 pages.
Synthes; 3.5 mm LCP Periarticular Proximal Humerus Plate; Apr. 2010; 22 pages.
Synthes; Locking Compression Plate (LCP) System (brochure); 2003; 6 pages.
Synthes, "Locking Compression Plate (LCP) System. Locking screw technology and conventional plating in one system;" 2003; 6 pages.
Synthes; Locking Compression Plate (LCP) System (brochure); Jan. 2007; 6 pages.
Synthes; Modular Mini Fragment LCP System (brochure); 2007; 12 pages.
Synthes; Small Fragment Locking Compression Plate (LCP) System (brochure); 2002; 43 pages.
Written Opinion of the International Searching Authority; International Application No. PCT/US2009/036211; Sep. 23, 2010; 8 pages.
"Zimmer® Universal Locking System," The Journal of Bone and Joint Surgery, vol. 89, No. 7, Jul. 2007, 1 page.
Zimmer, Inc. "Zimmer® Universal Locking System," brochure (2006), 4 pages.
Zimmer, Inc.; "Zimmer Universal Locking System;" brochure; 2009, 2 pages.
Zimmer, Inc. "Zimmer Holdings to Launch Innovative Locking Plate System at Orthopaedic Trauma Association Meeting," Sep. 14, 2006; 3 pages.
Zimmer, Inc.; "Zimmer Small Fragment Universal Locking System;" Surgical Technique; 2010; 16 pages.
Zimmer; Zimmer Periarticular Plating System-Low-Profile Fixation (catalog); 2003; 8 pages.

BONE PLATE FOR PLATE OSTEOSYNTHESIS AND METHOD FOR USE THEREOF

The present application is a divisional of application Ser. No. 13/840,194, filed Mar. 15, 2013 (U.S. Pat. No. 9,283,008), which claims the benefit of Provisional Application No. 61/738,141, filed Dec. 17, 2012; all of which are incorporated herein by reference.

BACKGROUND OF THE INVENTION

Field of the Invention

The present invention generally relates to a medical device and method for use thereof for facilitating reduction and repair of a fractured bone. More particularly, the present invention relates to a bone plate for use in osteosynthesis that affords use of at least two surgical approaches for repairing a fractured bone. More specifically, the present invention relates to a bone plate for osteosynthesis that is configured to facilitate utilization of a first surgical approach to attach at least a first portion of the bone plate to a fractured bone, and utilization of a second surgical approach to attach at least a second portion of the bone plate to the fractured bone Description of the Prior Art Not all fractures require surgical management, and of those that require surgery, there are a number of options to aid in healing of fractures including, pins, external fixators, intramedullary nails, plate osteosynthesis, etc. However, of these options, a very large number of fractures when treated surgically are in fact managed with plate osteosynthesis.

When approaching a fractured bone, the surgeon decides before surgery on a surgical approach; that is, the surgeon decides on a specific plan of attack for repairing the fractured bone during surgery. To illustrate, the surgeon will decide from an anatomic standpoint the direction that the fracture should be approached, e.g., anterior, posterior, medial, lateral, superior, inferior directions, or, for instance, antero-lateral, postero-lateral directions, etc. In general, the direction of approach to a fractured bone and a specific location along that particular bone has been well described in the anatomical and surgical literature—the direction of approach is not something that is developed de novo for every case. In other words, there are a number of a standard surgical approaches to suit just about all bone fractures. Therefore, a standard surgical approach will be chosen by the surgeon based on the fracture location along the bone. In addition, for the surgical approach decided upon, the surgeon will consider the skin incision and the consequences of making such an incision, the specific soft tissue structures to be encountered and protected during the dissection, and the access to be gained to the fracture itself.

When addressing a clavicle fracture, for example, the surgical approach will depend on the location of the fracture along the bone. To illustrate, for a fracture about the mid-shaft of the clavicle, it is not possible to approach the bone from a posterior direction. An easier approach for such a clavicle fracture may be from a superior direction. However, a problem with the superior approach for a fracture in the proximal end of the clavicle (i.e., closer to the sternum) is that the head and neck are in the way—therefore, access can be limited and it becomes more difficult to use a drill or screw driver or other necessary instrumentation for plate fixation. For a fracture in the proximal end of the clavicle, a surgical approach from a straight anterior direction provides more access. Furthermore, for a more lateral clavicle fracture, a surgical approach from the superior direction may be more suitable and easier to access.

All the bones in the body have such surgical approaches or road maps that allow the surgeon access to a specific fracture location along the bone. In many instances that access is quite limited and the risk of damage of critical nerves and soft tissues structures may be very high. For instance, one such approach is the posterior approach to the shaft of the humerus. The radial nerve is in close proximity to the humerus and in fact it wraps around the humeral shaft along a radial nerve groove. Any traction on the radial nerve usually leads to partial or total nerve injury. Additionally, for instance, making an incision to facilitate positioning of a plate on the antero-medial aspect of the mid-shaft of the tibia can result in wound breakdown and severe complications leading to infection and missing soft tissue coverage of the plate and the bone.

To adapt a conventional long bone plate to a complex fracture scenario, it is usually necessary to bend the plate or contour it to fit the anatomy. Given the typical robustness thereof, bending (or contouring) of conventional long bone plates in a complex fashion can be extremely difficult. Furthermore, helicoid and reconstruction plates are malleable to afford bending (or contouring) thereof in a complex fashion for a complex fracture scenario. However, helicoid and reconstruction plates are usually much weaker than conventional long bone plates, and can fail during axial loads prior to bone healing.

Adaption of plates may require complex three-dimensional synthesis on the part of the surgeon at the time of the surgery, and the time sensitive nature of surgery make it difficult to do so. Moreover, while conventional long bone plates are robust, such plates are difficult to bend (or contour). Furthermore, while helicoid and reconstruction plates are malleable to afford bending (or contouring) thereof, these plates are much weaker than conventional long bone plates.

Therefore, there is a need for a bone plate and a method for use thereof that attenuates the need for such three-dimensional synthesis during surgery, and additionally provides relatively robust structures for attachment to a fractured bone. As discussed below, the bone plate of the present invention can be as robust as conventional long bone plates, but also afford some of the dimensional advantages of helicoid and reconstruction plates. Furthermore, the bone plate and method for use thereof affords use of at least two surgical approaches to attach the bone plate to a fractured bone to facilitate reduction and repair thereof.

SUMMARY OF THE INVENTION

The present invention in a preferred embodiment contemplates a bone plate device for facilitating reduction and repair of a fractured bone, the bone plate device including a first domain, a second domain, and a transition zone between the first and second domains, the transitional zone spacing the first domain and the second domain apart from one another, the first domain including a length, a width perpendicular to the length, and a thickness perpendicular to the length and the width, the length of the first domain being greater than the width thereof, the width of the first domain being greater than the thickness thereof, the first domain extending in a first direction from the transition zone, and a portion of the first domain adjacent the transition zone being disposed in a first plane, the second domain including a length, a width perpendicular to the length, and a thickness perpendicular to the length and the width, the length of the second domain being greater than the width thereof, the width of the second domain being greater than the thickness thereof, the second domain extending in a second direction from the transition zone, and a portion of the second domain adjacent the transition zone being disposed in a second plane; the first and second directions being generally opposite from one another, the first domain having a first bone-contacting surface for contacting a portion of the fractured bone and the first domain having an opposite surface from the first bone-contacting surface, the second domain having a second bone-contacting surface for contacting another portion of the fractured bone and the second domain having an opposite surface from the second bone-contacting surface, and the transition zone including a first portion from which the first domain extends and a second portion from which the second domain extends, the first and second portions being angled with respect to one another such that the first and second planes of the first and second domains are generally transverse to one another.

The present invention in another preferred embodiment contemplates a method for surgically applying a bone plate to a fractured bone including providing the bone plate with a first domain, a second domain, and a transition zone between the first domain and the second domain, the transition zone spacing the first and second domains apart from one another, the first domain extending in a first direction from the transition zone, and a portion of the first domain adjacent the transition zone being disposed in a first plane, the second domain extending in a second direction from the transition zone, and a portion of the second domain adjacent the transition zone being disposed in a second plane, the first and second planes being generally transverse to one another; deforming or bending one of the first and second domains to accommodate the shape of the fractured bone; using a first surgical approach for reducing and repairing the fractured bone to apply the first domain to a first portion of the fractured bone; using a second surgical approach for reducing and repairing the fractured bone to apply the second domain to a second portion of the fractured bone; securing the first domain to the first portion of the fractured bone using a first fastener inserted into a fastener receiving hole formed in the first domain, and into the first portion of the fractured bone; and securing the second domain to the second portion of the fractured bone using a second fastener inserted into a fastener receiving hole formed in the second domain, and into the second portion of the fractured bone.

It is understood that both the foregoing general description and the following detailed description are exemplary and exemplary only, and are not restrictive of the invention as claimed.

BRIEF DESCRIPTION OF THE DRAWINGS

The accompanying drawings, which are incorporated in and constitute a part of the specification, illustrate preferred embodiments of the invention. Together with the description, they serve to explain the objects, advantages and principles of the invention. In the drawings.

DETAILED DESCRIPTION OF THE PREFERRED EMBODIMENT

The following description is intended to be representative only and not limiting, and many variations can be anticipated according to these teachings. Reference will now be made in detail to the preferred embodiments of this invention, examples of which are illustrated in the accompanying drawings.

Figure 1:
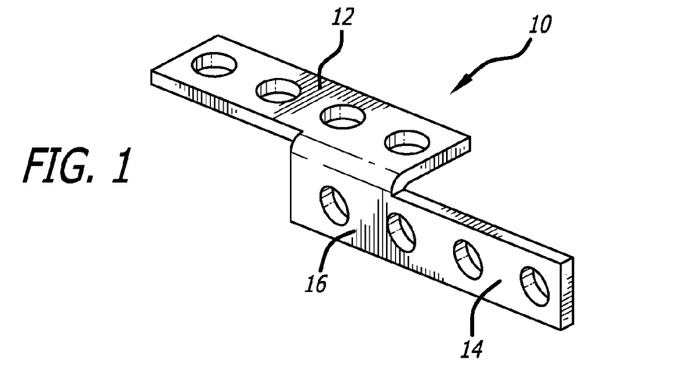
FIG. 1 depicts a representation of a first form of a bone plate according to the present invention.
Figure 2:
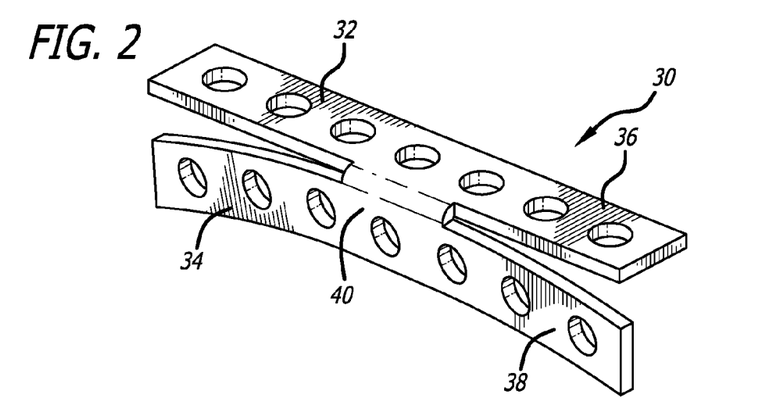
FIG. 2 depicts a representation of a second form of a bone plate according to the present invention.
Figure 3:
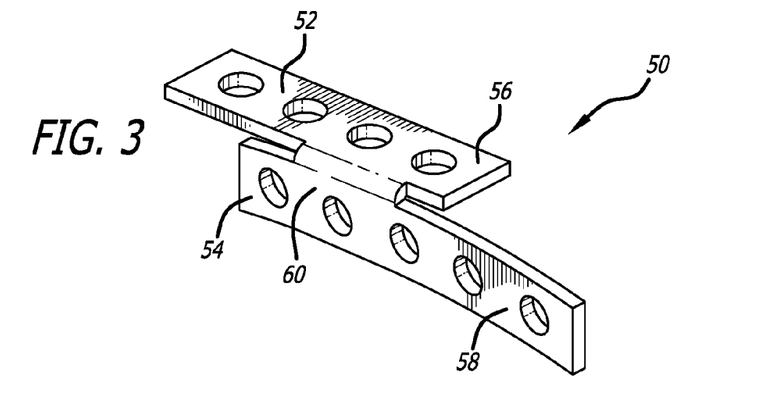
FIG. 3 depicts a representation of a third form of a bone plate according to the present invention.

FIGS. 1-3 depict representative forms of bone plates according to the present invention. The representative forms depicted in FIGS. 1-3 are generally indicated by the numerals 10, 30, and 50, respectively. As discussed below, the bone plates of the present invention can be modeled on the configurations of the representative forms 10, 30, and 50.

As depicted in FIGS. 1-3, the representative forms 10, 30, and 50 of the bone plates each include at least two domains extending in different directions from a transition zone. The directions in which each of the at least two domains extend are generally opposite, and the transition zone is configured to afford portions of the at least two domains to be substantially disposed in planes that are transverse to one another.

The at least two domains of the representative forms 10, 30, and 50 each correspond to different surgical approaches to attach the bone plates according to the present invention to a fractured bone. Each of the at least two domains include a bone contacting portion for contacting a different portion of the fractured bone. As such, a first domain of the at least two domains can be used in contacting a first portion of the fractured bone, and a second domain of the at least two domains can be used in contacting a second portion of the fractured.

As discussed above, the representative forms 10, 30, and 50 depicted in FIGS. 1-3 illustrate potential configurations for the bone plates of the present invention. Accordingly, the potential configurations of the bone plates according to the present invention can be adapted for use in reducing and repairing various fractured bones. For example, the bone plates according to the present invention can be used in reducing and repairing fractured humeri, fractured tibiae, and fractured clavicles (such as that depicted in FIGS. 5-7).

As depicted in FIG. 1, the representative form 10 includes a first domain 12, a second domain 14, and a transition zone 16 joining first and second domains 12 and 14 to one another. The first and second domains 12 and 14 extend in generally opposite directions. Furthermore, the transition zone 16 affords portions of the first and second domains 12 and 14 to be disposed in planes that are generally transverse to one another. For example, the planes in which portions of the first and second domains 12 and 14 can be angled generally perpendicular to one another, or oriented at other transverse angles relative to one another. For configurations of the bone plates according to the present invention generally modeled on the representative form 10, the transition zone 16 corresponds to portions of the bone anatomy that does not change significantly among bones of different individuals, and the first and second domains 12 and 14 correspond to portions of the bone anatomy that may require the first and second domains 12 and 14 to be bent or deformed to match the bone anatomy. However, bending or deforming of one of the first and second domains 12 and 14 will not necessarily affect the shape of the other of the first and second domains 12 and 14, and vice versa.

As depicted in FIG. 2, the representative form 30 includes a first domain 32, a second domain 34, a third domain 36, a fourth domain 38, and a transition zone 40 joining the first, second, third, and fourth domains 32, 34, 36, and 38 to one another. The first and second domains 32 and 34 extend in generally opposite directions from the third and fourth domains 36 and 38. Furthermore, the transition zone 40 affords portions of the first and third domains 32 and 36 to be disposed in planes that are generally transverse to the planes in which portions of the second and fourth domains 34 and 38 are disposed. For example, the planes in which portions of the first and third domains 32 and 36 are disposed can be angled generally perpendicular to the planes in which portions of the second and fourth domains 34 and 38 are disposed, or can be oriented at other transverse angles relative to one another. For configurations of the bone plates according to the present invention modeled on the representative form 30, the transition zone 40 corresponds to portion of the bone anatomy that does not change significantly among bones of different individuals, and the first, second, third, and fourth domains 32, 34, 36, and 38 correspond to portions of the bone anatomy that may require the first, second, third, and fourth domains, 32, 34, 36, and 38 to be bent or deformed to match the bone anatomy. However, bending or deforming of one of the first, second, third, and fourth domains, 32, 34, 36, and 38 will not necessarily affect the shape of the others of the first, second, third, and fourth domains, 32, 34, 36, and 38.

As depicted in FIG. 3, the representative form 50 includes a first domain 52, a truncated second domain 54, a truncated third domain 56, a fourth domain 58, and a transition zone 60 joining the first domain 52, the truncated second domain 54, the truncated third domain 56, and the fourth domain 58 to one another. The first domain 52 and the truncated second domain 54 extend in generally opposite directions from the truncated third domain 56 and the fourth domain 58. Furthermore, the transition zone 40 affords portions of the first domain 52 and the truncated third domain 56 to be disposed in planes that are generally transverse to the planes in which portions of the truncated second domain 54 and the fourth domain 58 are disposed. For example, the planes in which portions of the first domain 52 and the truncated third domain 56 are disposed can be angled generally perpendicular to the planes in which portions of the truncated second domain 54 and the fourth domain 58 are disposed, or can be oriented at other transverse angles relative to one another. For configurations of the bone plates according to the present invention modeled on the representative form 50, the transition zone 60 corresponds to the portion of the bone anatomy that does not change significantly among bones of different individuals, and the first domain 52, the truncated second domain 54, the truncated third domain 56, and the fourth domain 58 correspond to portions of the bone anatomy that may require the first domain 52, the truncated second domain 54, the truncated third domain 56, and the fourth domain 58 to be bent or deformed to match the bone anatomy. However, bending or deforming of one of the first domain 52, the truncated second domain 54, the truncated third domain 56, and the fourth domain 58 will not necessarily affect the shape of the others of the first domain 52, the truncated second domain 54, the truncated third domain 56, and the fourth domain 58.

Furthermore, the bone plates according to the present invention could include three domains. For example, a bone plate according to the present invention could have a configuration modeled on representative form 30 with one of the first, second, third, and fourth domains 32, 34, 36, and 38 removed therefrom.

Figure 4:
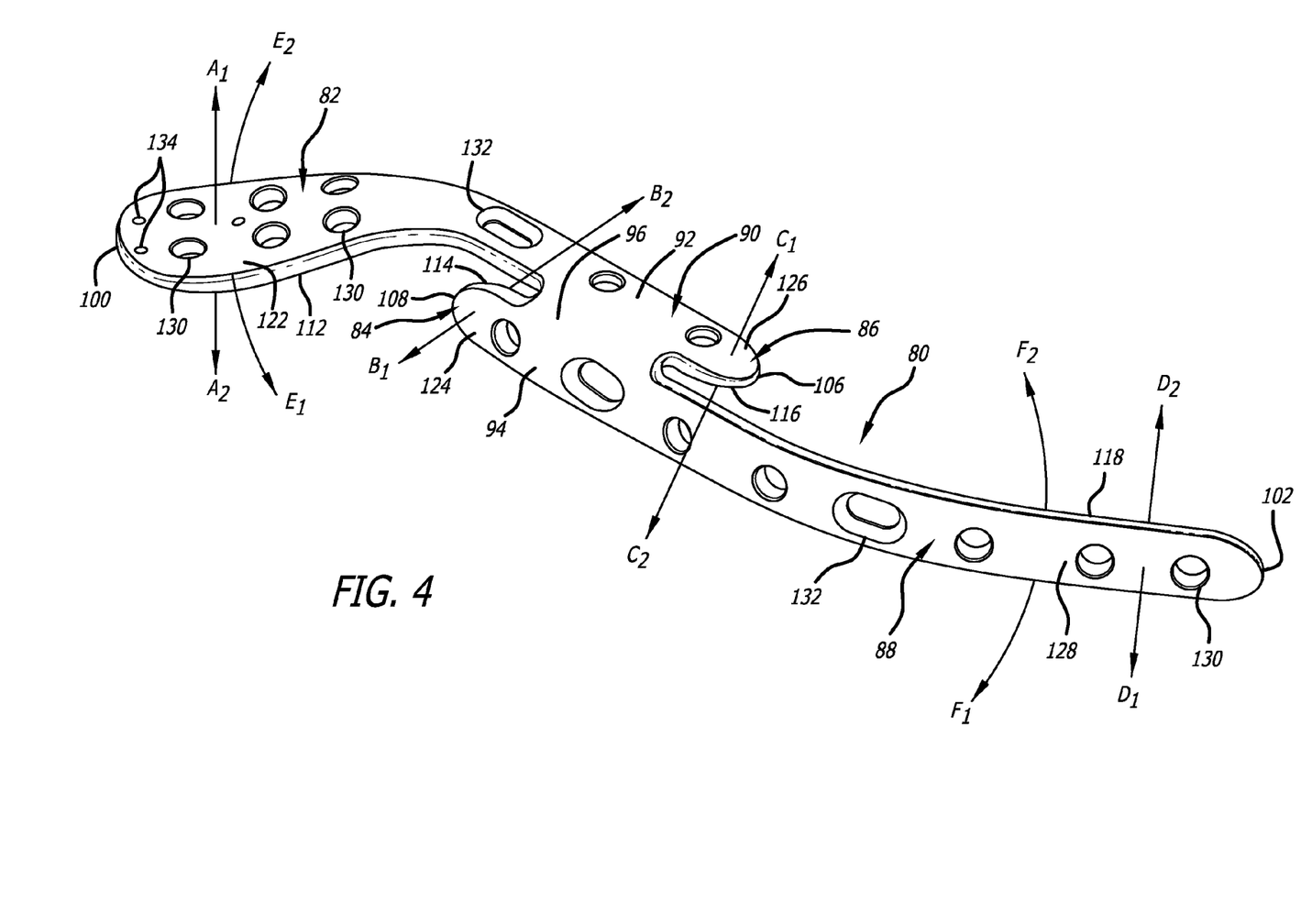
FIG. 4 depicts a perspective view a first illustrative embodiment of a bone plate according to the present invention for attachment to a fractured bone, the first illustrative embodiment incorporates a first domain facilitating attachment to a first portion of the fractured bone and incorporates a second domain facilitating attachment to a second portion of the fractured bone.

A first illustrative embodiment of a bone plate generally modeled on the representative form 50 described above is generally indicated by the numeral 80 in FIG. 4. The bone plate 80 is provided for reduction and repair of a fractured bone, and includes a first domain 82, a second truncated domain 84, a third truncated domain 86, and a fourth domain 88. The second and third domains 84 and 86 are truncated relative to the first and fourth domains 82 and 88. A transition zone 90 joins the first domain 82, the truncated second domain 84, the truncated third domain 86, and the fourth domain 88 to one another. The transition zone 90 includes a first portion 92, a second portion 94, and a bend 96 between the first and second portions 92 and 94. The first and second portions 92 and 94 are angled with respect to one another, and the angularity thereof serves in resisting deformation of the bone plate 80 at the transition zone 90.

As depicted in FIG. 4, the first domain 82 and the truncated second domain 84 extend in generally opposite directions from the truncated third domain 86 and the fourth domain 88. Furthermore, the transition zone 90 affords portions of the first domain 82 and the truncated third domain 86 to be disposed in planes that are generally transverse to the planes in which portions of the truncated second domain 84 and the fourth domain 88 are disposed. For example, the planes in which portions of the first domain 82 and the truncated third domain 86 are disposed can be angled generally perpendicular to the planes in which portions of the truncated second domain 84 and the fourth domain 88 are disposed, or can be oriented at other transverse angles relative to one another. As such, as depicted in FIG. 4, the first domain 82 and the truncated third domain 86 extend in generally opposite directions from the first portion 92 of the transition zone 90, and the truncated second domain 84 and the fourth domain 88 extend in generally opposite directions from the second portion 94 of the transition zone 90.

The bone plate 80 includes a first end 100 provided on a distal most portion of the first domain 82 from the transition zone 90, and includes a second end 102 provided on a distal most portion of the fourth domain 88 from the transition zone 90. The length of the bone plate 80 is between the first end 100 and the second end 102 thereof.

The bend 96 of the transition zone 90 (depending on material selection) may afford limited deformation thereof in at least one direction transverse to the length of the bone plate 80. However, the bend 96 will resist deformation along its portion of the length of the bone plate 80. As such, the transition zone 90 provides rigidity to the bone plate 80. Typically, the transition zone 90 will correspond to the portion of the bone anatomy that does not change significantly among bones of different individuals.

In addition to the length of the bone plate 80, the first domain 82, the first portion 92, and the truncated third domain 86 have a length associated therewith, and the truncated second domain 84, the second portion 94, and the fourth domain 88 have a length associate therewith. The length of the first domain 82, the first portion 92, and the truncated third domain 86 is between the first end 100 of the bone plate 80 and an end 106 of the truncated third domain 86. The length of the truncated second domain 84, the second portion 94, and the fourth domain 88 is between the second end 102 of the bone plate 80 and an end 108 of the truncated second domain 84.

The first domain 82 and the truncated third domain 86 are bendable or deformable in directions $A_1$ and $A_2$, and directions $C_1$ and $C_2$, respectively, along their portions of the length between the first end 100 of the bone plate 80 and end 106; and the truncated second domain 84 and the fourth domain 88 are bendable or deformable in directions $B_1$ and $B_2$, and directions $D_1$ and $D_2$, respectively, along their portions of the length between the second end 102 of the bone plate 80 and the end 108. Thus, while the deformation of the bone plate 80 is limited along the transition zone 90, the first domain 82, the truncated second domain 84, the truncated third domain 86, and the fourth domain 88 can be bent or deformed to the contours of a bone. For example, as depicted in FIG. 4, the fourth domain 88 is bent or deformed in the direction $D_2$ to accommodate the shape of a fractured bone.

The first domain 82, the truncated second domain 84, the truncated third domain 86, and the fourth domain 88 include first surfaces 112, 114, 116, and 118, respectively, for placement against the fractured bone, and opposite second surfaces 122, 124, 126, and 128. The first surfaces 112, 114, 116, and 118 can be concave to accommodate the contour of the fractured bone, and the second surfaces 122, 124, 126, and 128 can be convex to prevent irritation of soft tissues adjacent the fractured bone.

The thicknesses of the first domain 82, the truncated second domain 84, the truncated third domain 86, and the fourth domain 88 between the first surfaces 112, 114, 116, and 118, and the second surfaces 122, 124, 126, and 128, respectively, can be varied. Furthermore, the widths of the first domain 82, the truncated second domain 84, the truncated third domain 86, and the fourth domain 88 perpendicular to the thickness thereof can be varied along the length of the bone plate 80 between the first and second ends 100 and 102. As such, the dimensions of the first surfaces 112, 114, 116, and 118, and the second surfaces 122, 124, 126, and 128 can correspondingly be varied. For example, as depicted in FIG. 4, the widths of the truncated second domain 84, the truncated third domain 86, and the fourth domain 88 are uniform along the length of the bone plate 80, and the width of the first domain 82 increases from the transition zone 90 to the end 100 of the bone plate 80.

In addition to being bendable or deformable in directions $A_1$, $A_2$, $B_1$, $B_2$, $C_1$, $C_2$, $D_1$, and $D_2$, the first domain 82 and the truncated third domain 86 can (depending on material selection) be bent or deformed in planes perpendicular to the thicknesses thereof in which the lengths thereof pass; and the second truncated domain 84 and the fourth domain 88 can (depending on material selection) be bent or deformed in planes perpendicular to the thicknesses thereof in which the lengths thereof pass. For example, the first domain 82 is bendable or deformable in directions $E_1$ and $E_2$, and the fourth domain 88 is bendable or deformable in directions $F_1$ and $F_2$. To illustrate, as depicted in FIG. 4, the first domain 82 is bent or deformed in the direction $E_1$ to accommodate the shape of a fractured bone.

Besides being bendable or deformable as described above, the first domain 82, the truncated second domain 84, the truncated third domain 86, and the fourth domain 88 can (depending on the material selection) be somewhat twisted to accommodate the shaft of a fractured bone. To illustrate, bending or deforming the fourth domain 88 in one of the directions $F_1$ and $F_2$ in addition to the bend or deformation in the direction $D_2$ could provide such a twist to the fourth domain 88.

Various apertures are formed in the first domain 82, the truncated second domain 84, the truncated third domain 86, and the fourth domain 88 between the first surfaces 112, 114, 116, and 118, and second surfaces 122, 124, 126, and 128, respectively. For example, the bone plate 80 includes apertures 130 and apertures 132 provided therealong for receipt of fasteners (such as fasteners 140 and 142 shown in FIGS. 5-7) that can used to facilitate attachment of the bone plate 80 to a fractured bone. The apertures 130 and 132 can have various sizes and shapes—as depicted in FIG. 4, the apertures 130 are circular or rounded, and the apertures 132 are elongated with rounded end portions. Furthermore, the bone plate 80 includes apertures 134 for receiving pins (not shown) to facilitate temporary placement of the bone plate 80 with respect to a fractured bone.

The heads and shafts of the fasteners (such as fasteners 140 and 142 shown in FIGS. 5-7) can be received in the apertures 130 and 132, and can have various lengths and have different sizes and shapes (e.g., be configured to have cylindrical or frusto-conical shaped head portions). The heads can be provided with or without threads facilitating engagement with complimentary structures provided in the bone plate 80. Furthermore, the shafts can be provided with regular roughened or rough surfaces (hereinafter regular roughened surfaces), irregular roughened or rough surfaces (hereinafter irregular roughened surfaces), and/or smoothened or smooth surfaces (hereinafter smoothened surfaces). The regular roughened surfaces are repeating patterns of surface protrusions or indentations (such as threads, ratchets, or similar structures), and the irregular roughened surfaces (such as barbs or similar structures) are non-repeating surface protrusions or indentations. The surfaces of the shafts can serve in preventing withdrawal of the fasteners from the fractured bone.

While the first domain 82, the truncated second domain 84, the truncated third domain 86, and the fourth domain 88 are discussed above, the bone plate 80 could have been formed with any one of the domains being elongated or truncated, with more or less than four domains, and with domains having larger or smaller dimensions than those depicted in FIG. 4. For example, the bone plate 80 could be modeled on the representative form 30 to have two domains by not including the truncated second and third domains 84 and 86. Furthermore, the bone plate 80 could be modeled on the representative form 50 to include domains (in place of the truncated second and third domains 84 and 86) having dimensions similar to those of the first and fourth domains 82 and 88.

Each of the domains of the bone plate 80 can be used to facilitate use of different surgical approaches for attaching the bone plate 80 to a fractured bone. For example, the first domain 82 affords a superior surgical approach to a fractured bone, and the fourth domain 88 affords an anterior surgical approach to a fractured bone. However, the configuration of the bone plate 80 is not limited thereto. The bone plate 80 can, for example, be configured to afford various combinations of surgical approaches from anterior, posterior, medial, lateral, superior, and inferior directions. The bone plate 80 allows a surgeon to make use of well described knowledge in terms of surgical approaches and to combine such approaches in order to facilitate the application of the bone plate 80 to a fractured bone, while minimizing risk and hazards of applying the bone plate 80 using a single surgical approach.

Figure 5:
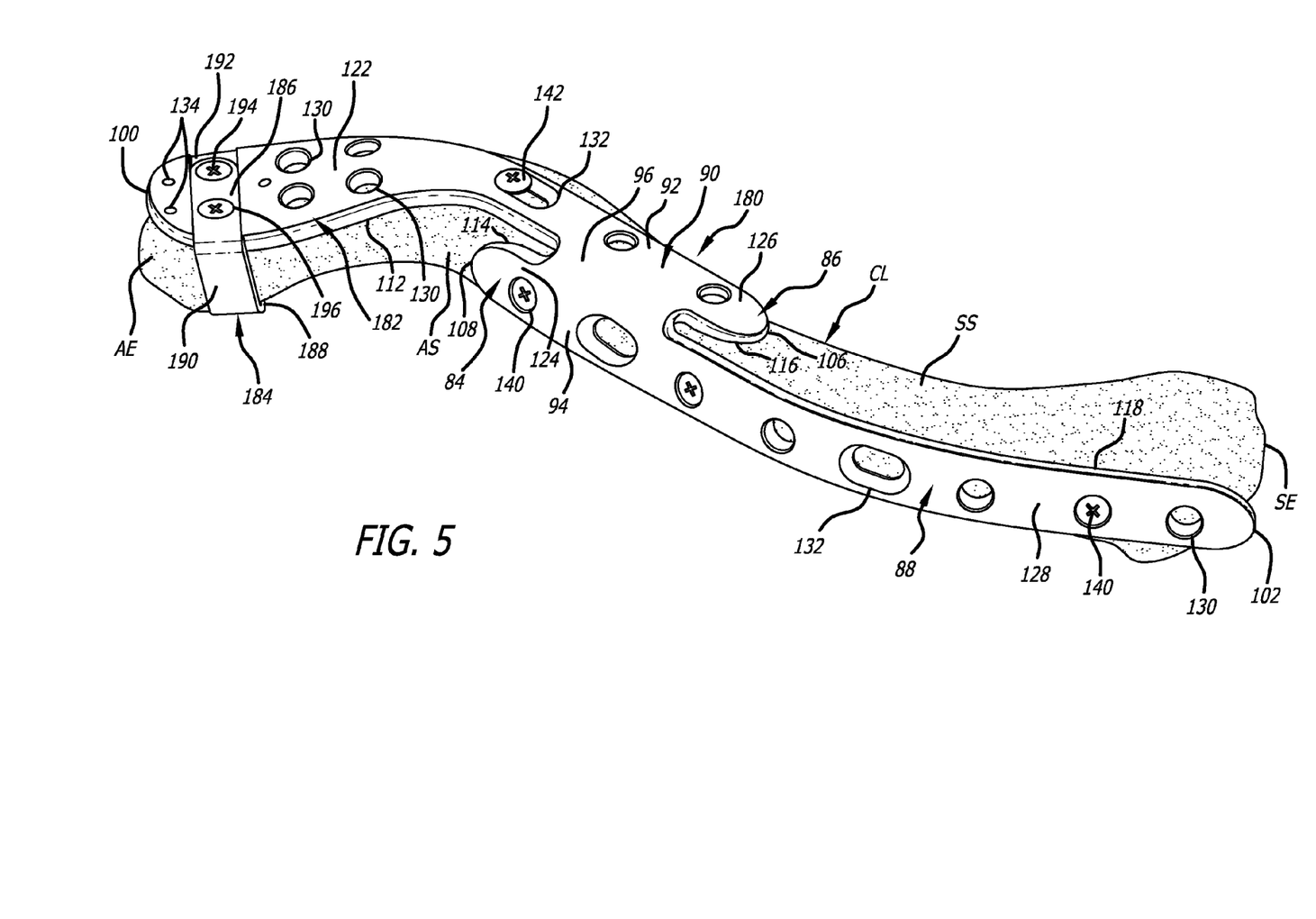
FIG. 5 depicts a first perspective view of a second illustrative embodiment of a bone plate according to the present invention in position with respect to a fractured bone, the second illustrative embodiment incorporates a first domain facilitating attachment to a first portion of the fractured bone and incorporates a second domain facilitating attachment to a second portion of the fractured bone.
Figure 6:
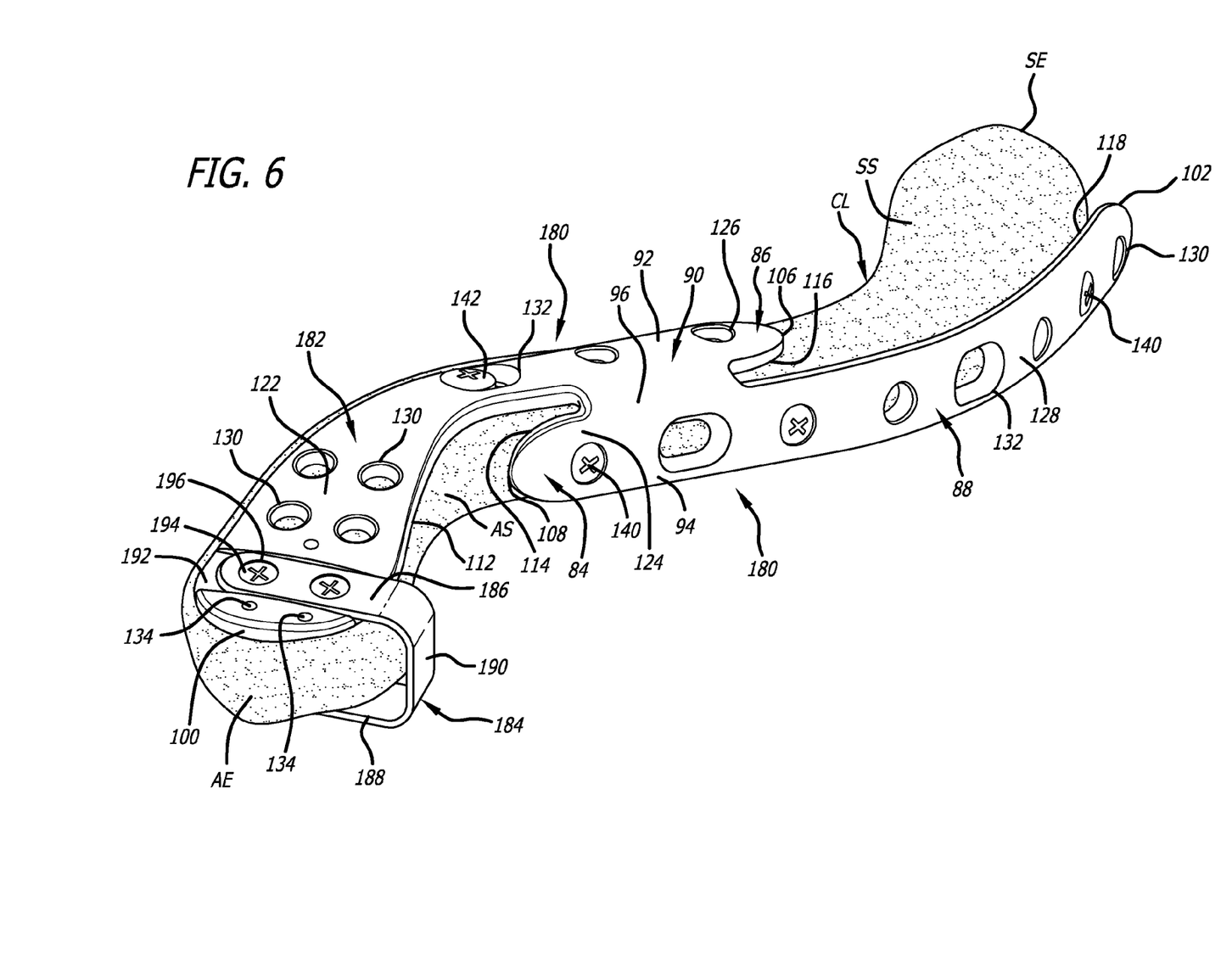
FIG. 6 depicts a second perspective view of the second illustrative embodiment of the bone plate depicted in FIG. 5 positioned with respect to the fractured bone.
Figure 7:
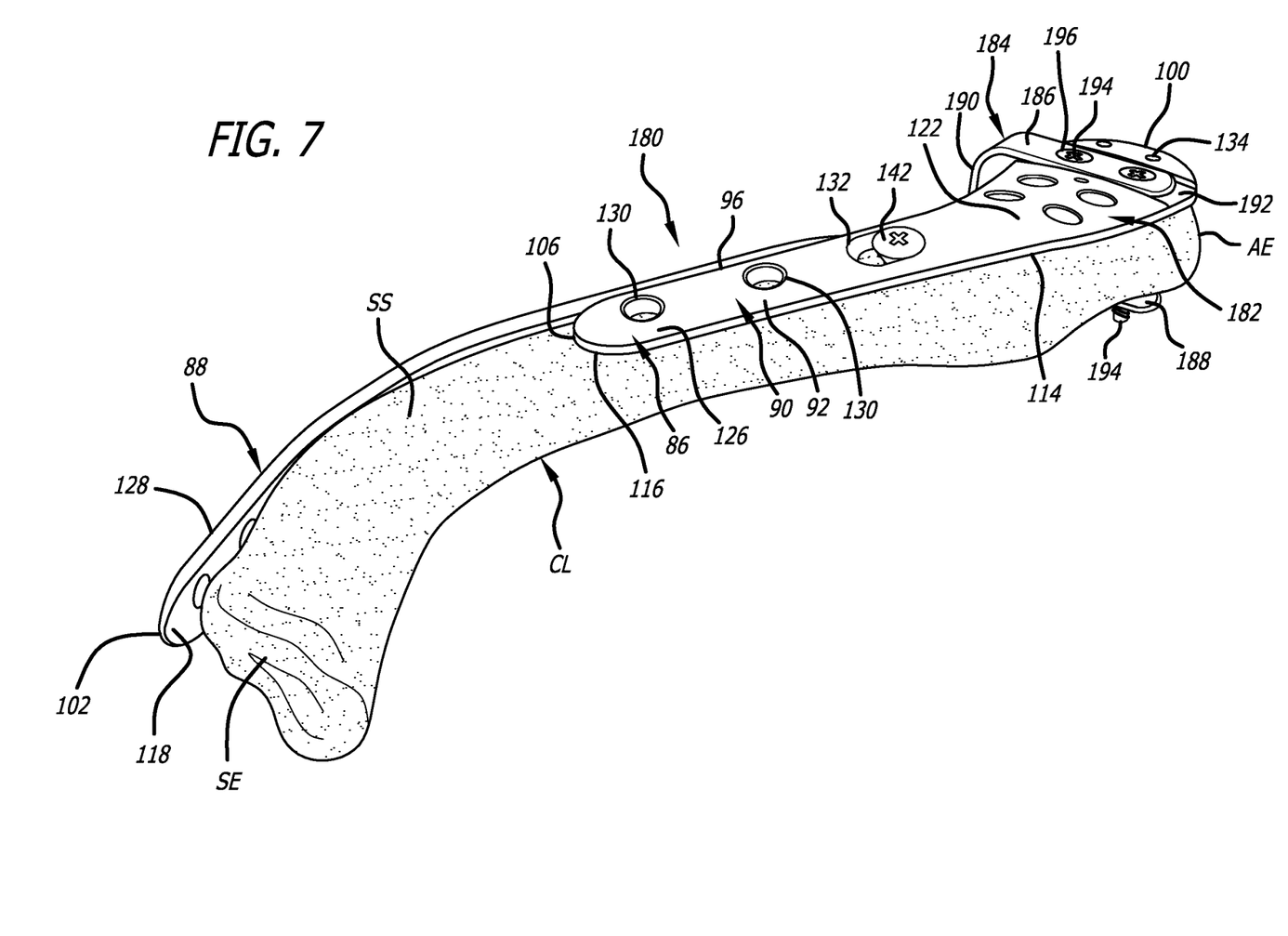
FIG. 7 depicts a third perspective view of the second illustrative embodiment of the bone plate depicted in FIGS. 5 and 6 positioned with respect to the fractured bone.

FIGS. 5-7 depict a bone plate 180 in position with respect to a fractured clavicle CL. Except for portions of a first domain 182 and use of a c-clamp 184, the bone plate 180 is identical to the bone plate 80 and can include the features thereof. Thus, like numbering will be used in indicating like features of the bone plate 180 in FIGS. 5-7 and as discussed below. To illustrate, the bone plate 180 (like the bone plate 80) includes the truncated second domain 84, the truncated third domain 86, and the fourth domain 88, and the corresponding features thereof.

As depicted in FIGS. 5-7, the clavicle CL includes a superior surface SS, an anterior surface AS, and an acromial extremity AE and a sternal extremity SE at opposite ends thereof. Furthermore, as depicted in FIGS. 5-7, the first domain 182 is positioned on superior surface SS and extends from the adjacent the middle of the clavicle CL to adjacent the acromial extremity AE; and the fourth domain 88 is positioned on the anterior surface AS and extends from adjacent the middle of the clavicle CL to adjacent the sternal extremity SE.

The bone plate 180 is not limited to the configuration depicted in FIGS. 5-7. Like the bone plate 80, the bone plate 180 can have various configurations, and such configurations can afford various combinations of surgical approaches (e.g., anterior, posterior, medial, lateral, superior, and inferior directions) to apply the bone plate 180 to a fractured bone, like the clavicle CL.

The first domain 182 of the bone plate 180 is configured to facilitate engagement of the c-clamp 184 therewith. The c-clamp 184 is used to further strengthen the attachment of the first domain 182 to the clavicle CL. The c-clamp 184 is similar to those disclosed in U.S. patent application Ser. No. 13/411,069, which is incorporated by reference herein. The c-clamp 184 includes a first leg portion 186, a second leg portion 188, and a connecting portion 190 connecting the first leg portion 186 and the second leg portion 188 to one another. To facilitate engagement with the c-clamp 184, the first domain 182 can include a recess 192 for receiving at least a portion of the first leg portion 186 therein. The connecting portion 190 has a length permitting the c-clamp 184 to bridge the clavicle CL and the first domain 182. As depicted in FIGS. 5-7, the first leg portion 186 engages the first domain 182 (and the recess 192 thereof), and the second leg portion 188 engages the clavicle CL.

In addition to fasteners 140 and 142 that can be used to secure the bone plate 180 in position on the clavicle CL, fasteners 194 can be used to attach the c-clamp 184, the bone plate 180, and clavicle CL to one another. The fasteners 194 can be received through apertures 196 formed in the first leg portion 186 of the c-clamp 184, through corresponding apertures (not shown) provided in the first domain 182, and into the clavicle CL. The fasteners 194 can include the features of the fasteners 140 and 142, and be long enough to (as depicted in FIG. 7) extend through the clavicle CL to extend through apertures (not shown) formed in the second leg portion 188 of the c-clamp.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

I claim:

1. A method for surgically applying a bone plate to a fractured bone comprising:
   providing the bone plate with a first domain, a second domain, and a transition zone between the first domain and the second domain, the transition zone spacing the first and second domains apart from one another, the first domain extending in a first direction from the transition zone, and a portion of the first domain adjacent the transition zone being disposed in a first plane, the second domain extending in a second direction from the transition zone, and a portion of the second domain adjacent the transition zone being disposed in a second plane, the first and second planes being generally transverse to one another;
   deforming or bending one of the first and second domains to accommodate the shape of the fractured bone;
   using a first surgical approach for reducing and repairing the fractured bone to apply the first domain to a first portion of the fractured bone;
   using a second surgical approach for reducing and repairing the fractured bone to apply the second domain to a second portion of the fractured bone;
   securing the first domain to the first portion of the fractured bone using a first fastener inserted into a fastener receiving hole formed in the first domain, and into the first portion of the fractured bone; and
   securing the second domain to the second portion of the fractured bone using a second fastener inserted into a fastener receiving hole formed in the second domain, and into the second portion of the fractured bone.

2. The method according to claim 1, wherein the first and second domains each include a length, a width perpendicular to the length, and a thickness perpendicular to the length and the width, the lengths of the first and second domains being greater than the widths thereof, the widths of the first and second domains being greater than the thicknesses thereof, the first and second domains each being deformable or bendable in directions parallel to the thicknesses thereof.

3. The method according to claim 2, wherein the first and second domains are each deformable or bendable in directions perpendicular to the thicknesses thereof.

4. The method according to claim 1, further comprising using a third surgical approach to apply a third domain of the bone plate to the fractured bone.

5. The method according to claim 4, further comprising using a fourth surgical approach to apply a fourth domain of the bone plate to the fractured bone.

6. The method according to claim 5, wherein the third and fourth domains are spaced apart from one another, and from the first and second domains.

* * * * *